United States Patent [19]

Bidwell et al.

[11] Patent Number: 5,673,696
[45] Date of Patent: Oct. 7, 1997

[54] ULTRASOUND TRANSDUCER PROBE HOLDER

[75] Inventors: Dean J. Bidwell; Stephen B. Hooper, both of Redmond; Andrew L. Walston; Anthony P. Grasso, both of Seattle, all of Wash.

[73] Assignee: Siemens Medical Systems Inc., Iselin, N.J.

[21] Appl. No.: 535,498

[22] Filed: Sep. 28, 1995

[51] Int. Cl.[6] .................................................. A61B 8/00
[52] U.S. Cl. ........................................................ 128/660.01
[58] Field of Search .......................... 128/660.01, 660.1, 128/662.03; 73/622, 633

[56] References Cited

U.S. PATENT DOCUMENTS 4,215,585  8/1980  Kunii et al. .............................. 73/633
4,612,808  9/1986  McKirdy et al. ........................ 73/622
5,505,203  4/1996  Deitrich et al. .................... 128/660.01

Primary Examiner—George Manuel

[57] ABSTRACT

A probe holder embodies an insert body removably set into a through-slot of an ultrasound system panel. The holder defines an inner cavity extending from a first opening at a top surface to a second opening at a bottom surface. A side opening extends the axial length of the holder from the first opening to the second opening. Upon insertion of the holder into the panel through-slot, the holder is movable between an open position and a closed position. At the open position the holder side opening is aligned with a corresponding side opening of the panel. With the holder moved into the closed position, the holder side opening is blocked by inner walls of the panel through-slot. A probe cord slides through the side openings while the holder is in the open position. Once the holder is moved to the closed position, the probes cord is radially trapped within the holder.

11 Claims, 7 Drawing Sheets

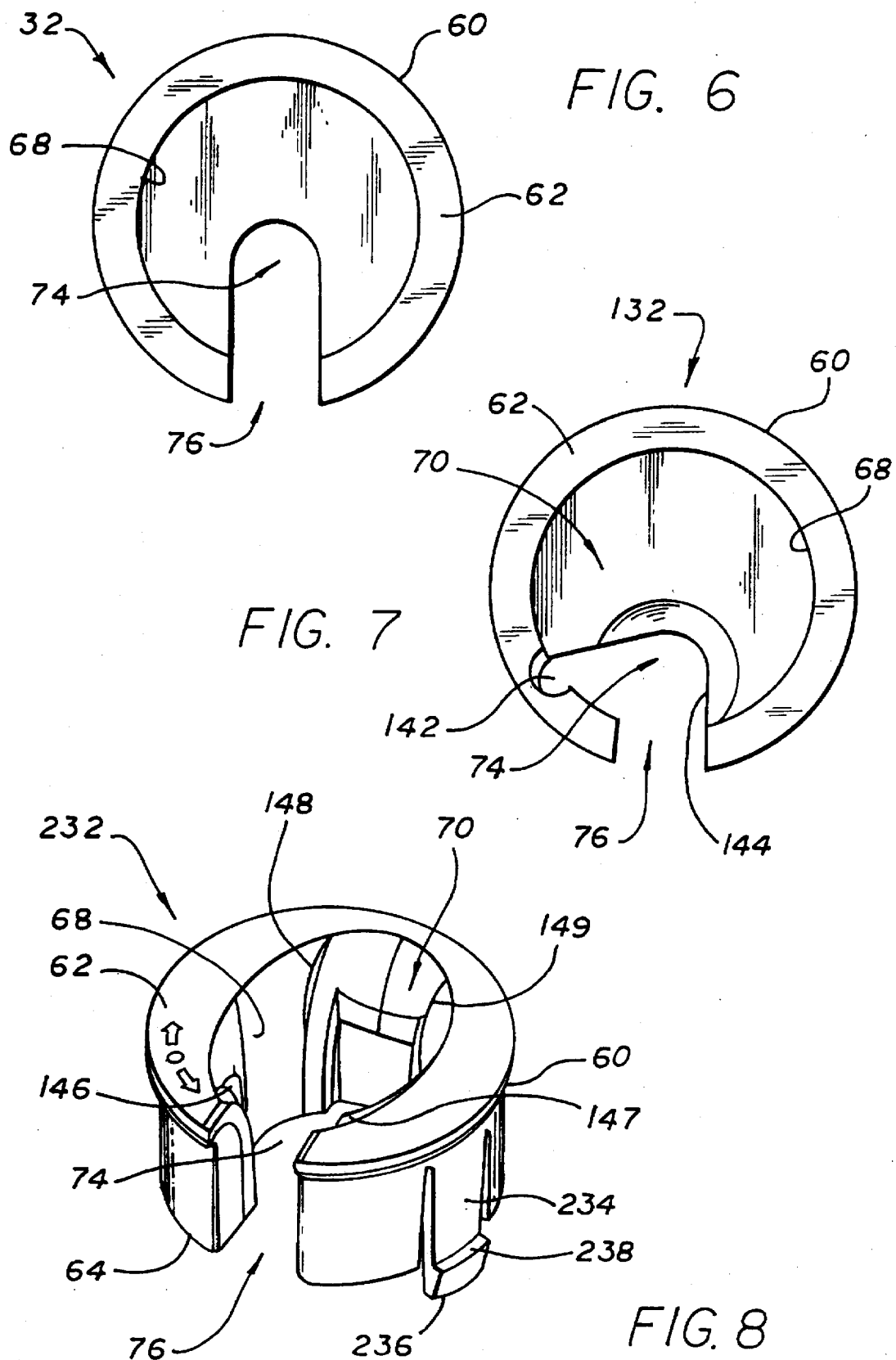

ULTRASOUND TRANSDUCER PROBE HOLDER

BACKGROUND OF THE INVENTION

This invention relates generally to apparatus for easing access to and storage of ultrasound transducer probes.

An ultrasound medical diagnostic imaging system generate images of anatomical structures within a patient's body by scanning a target area with ultrasound signals. An ultrasound transducer probe is held and manipulated by an operator during the scan. Typically, ultrasound signals on the order of typically 3.0 to 10.0 MHz are transmitted via the probe into a patient. Returning echo signals then are received at the probe, formed into a beam-pattern and analyzed to convey image and/or flow characteristics of the scanned area.

Scanning different target areas of a patient may involve using different transducer probes having differently-shaped transducers. Accordingly, an ultrasound system typically has several probes. A probe typically includes a transducer within a housing coupled to the main body of the ultrasound system via an electric cord. Each probe typically rests within a holder at the edge of an input panel accessible by the operator. FIG. 1 shows a conventional probe holder 12 integral to the ultrasound system 10. The holder 12 is a cylindrical opening through a panel 13 having a depth of approximately 3-5 centimeters. Other shapes such as rectangular cylinders also are known. A side opening 14 occurs along the cylindrical wall as shown. To store the transducer probe 16, a user moves the probe cord 18 through the side opening 14. The probe 16 is then slid downward through the holder 12. The head 20 of the probe where the transducer is housed typically has a width exceeding the diameter of the holder's cylindrical opening. As the probe 16 is slid into the cylindrical opening, the transducer head 20 comes to rest at the top of the opening. The probe head 20 typically is unable to fit through the cylindrical opening. Often three or more holders 12 are positioned along a panel holding respective probes.

An ultrasound machine typically is movable so the operator can get the best position when scanning a patient. A problem with prior probe holders has been that probes readily fall out of the probe holder through the side opening. This is a common problem which has been very annoying to operators. Once the probes fall out, their cords easily become tangled. Accordingly, there is need for a more effective probe holder.

Differing probes of the ultrasound system often are of a different size. As a result, the prior probe holder openings have been of differing size. A given probe fits within a given opening. In practice, therefore each probe has had a dedicated probe holder. An operator, however, may use one probe more regularly than other probes and prefer a different probe holder arrangement. Because the probe holders are integral to the system panel, rearranging the probes would leave one or more probes with a poorer fit—and be more likely to fall out.

SUMMARY OF THE INVENTION

According to the invention, a probe holder embodies an insert body removably set into a through-slot of an ultrasound system panel.

According to one aspect of the invention, each of multiple through-slots at the interface panel are of a common, uniform size. In addition each of multiple insert bodies serving as respective probe holders have a common outer dimension. As a result, each of the multiple probe holders fits any of the multiple through-slots.

According to another aspect of the invention, various probe holder embodiments have differing internal dimensions for holding differing ultrasound probes. A large probe has a corresponding probe holder with a large inner cavity. a smaller probe has a corresponding probe holder with a smaller inner cavity. The operator can insert the probe holders in any through-slot. Thus, the operator can arrange the holders and probes to one's desired preference.

Each probe holder body defines an inner cavity and has a top surface with a first opening to the inner cavity and a bottom surface with a second opening to the inner cavity. A side opening to the inner cavity occurs along an outer wall and extends from the top opening to the bottom opening.

According to another aspect of the invention, the probe holder includes an open position and a closed position. While in the open position, a transducer probe is inserted in the probe holder. Specifically a probe's cord is moved through the side opening of the system panel and the side opening of the holder body into the inner cavity. The probe holder then is adjusted to the closed position. In the closed position, the holder's side opening is moved out of alignment with the panel's side opening. Instead the holder's side opening is exposed to an inner wall of the panel through-slot. Thus, the probe cord is radially trapped with the inner cavity. The probe cord slides axially through the inner cavity until the probe head reaches the cavity. The probe header is too large to fit through the inner cavity and comes to rest at the top opening to the inner cavity. The probe is then secure.

According to another aspect of the invention, the probe holder rotates within the panel through slot. The probe holder open position is defined as the position with the probe holder side opening aligned with the through-slot side opening. The probe holder is rotated within the through-slot to move the side openings out of alignment when adjusting to the closed position.

According to another aspect of the invention the probe holder has an inner surface shaped to receive a probe at a given orientation. Once the probe is inserted and comes to rest in the holder, the probe is rotated by the user. This in turn rotates the probe holder from the open position to the closed position.

According to another aspect of the invention, the probe holder includes grip surfaces for the user to rotate the probe holder between the open and closed position.

According to another aspect of the invention, the probe holder includes a ridge extending the axial length of an outer wall of the holder. The ridge is positioned within the panel through-slot and is adjacent to the holder side opening. The ridge limits the rotation of the probe holder. In the open position the ridge meets one edge of the panel side walls that define the panel side opening. In the closed position the ridge meets an edge of an opposing panel wall defining the panel side opening.

According to another aspect of the invention, the probe holder includes protrusions extending radially inward within the inner cavity. The protrusions allow a probe cord to slide through the inner cavity, but block a narrow probes path.

One advantage of the invention is that an operator can arrange the probes according to desired preference. The probe holders are interchangeable among through-slots at the ultrasound system panel. Another advantage is that the probes are secured in place preventing them from falling and getting tangled. Another advantage is that the holders, being removable, are accessible and convenient for easier cleaning.

BRIEF DESCRIPTION OF THE DRAWINGS

FIG. 6 is a top view of a probe holder according to an embodiment of this invention;

FIG. 7 is a top view of a probe holder according to another embodiment of this invention;

FIG. 8 is a perspective view of a probe holder according to another embodiment of this invention;

DESCRIPTION OF SPECIFIC EMBODIMENTS

Ultrasound System Panel

Figure 1:
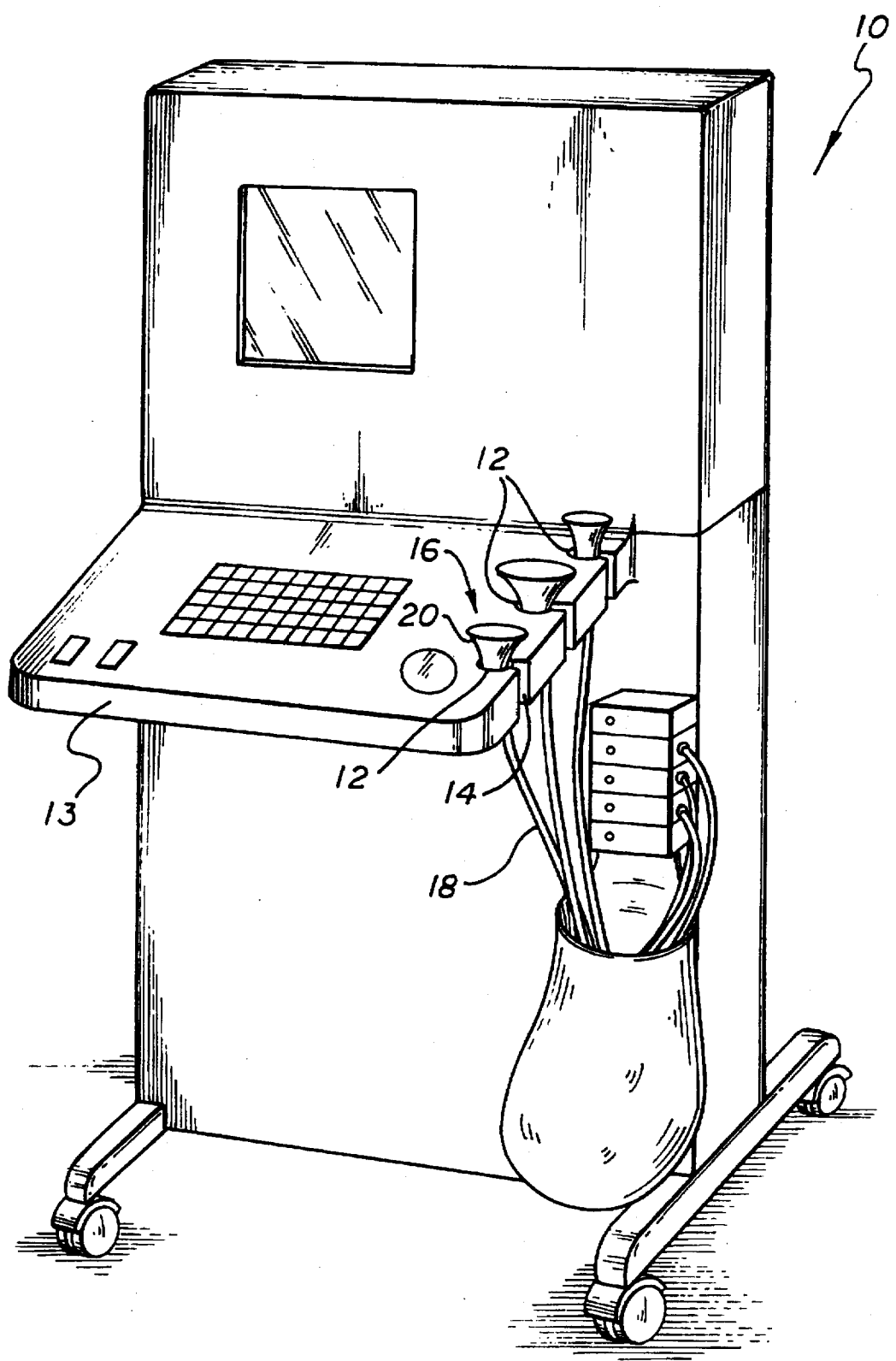
FIG. 1 is a perspective view of an ultrasound medical imaging system having conventional probe holders integral to the system panel.
Figure 2:
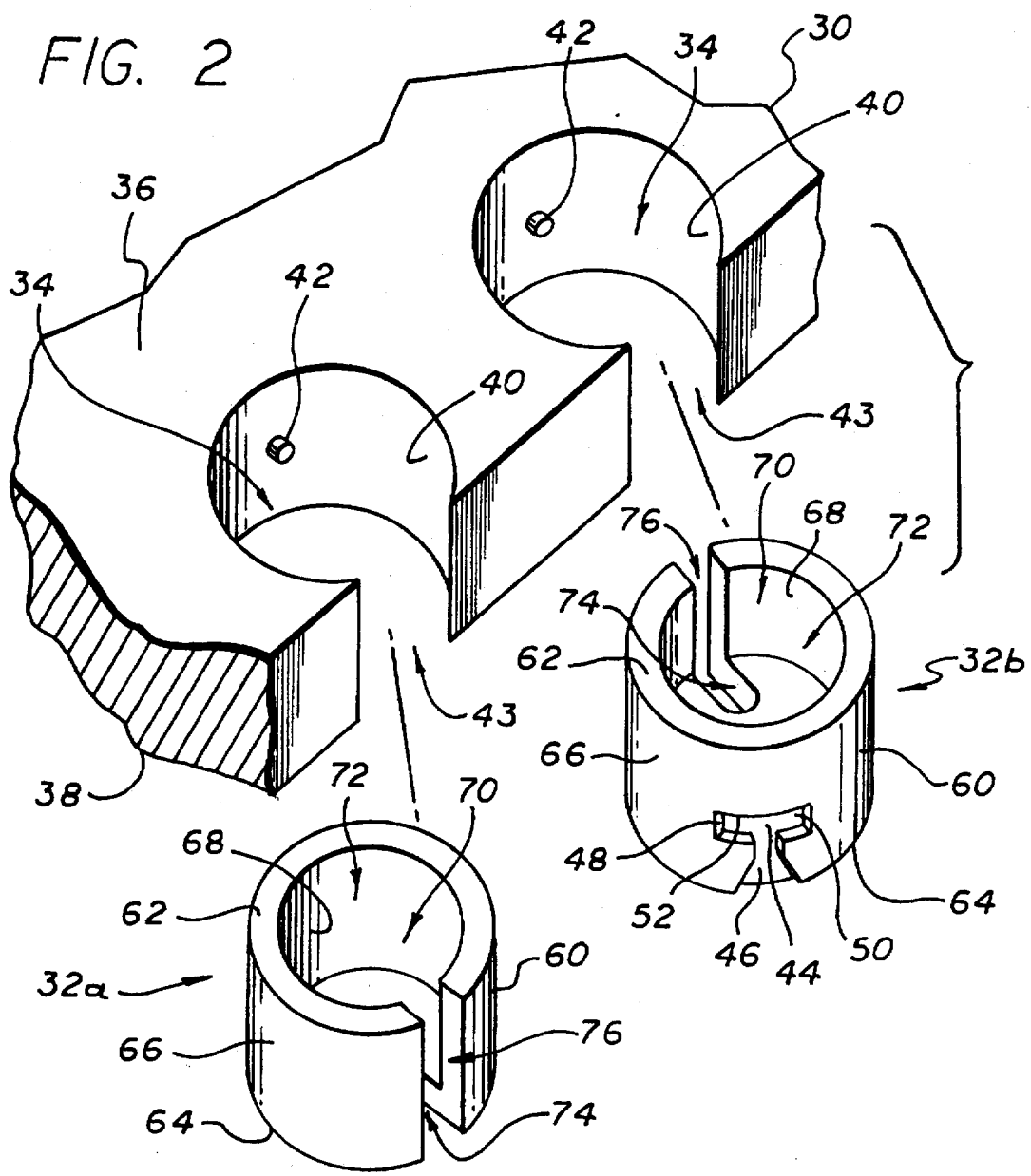
FIG. 2 is a partial view of an ultrasound system panel and removable ultrasound probe holders according to an embodiment of this invention.

FIG. 2 shows a portion of an ultrasound system panel 30 and two insertable probe holders 32a,b according to an embodiment of this invention. In one embodiment the panel 30 is part of an ultrasound system serving a similar function as the conventional panel 13 in FIG. 1. The panel 30 serves as part of an operator interface. In other embodiments the panel 30 is part of the main body or another portion of the ultrasound system. For example, in other embodiments the panel is part of an arm protruding from the ultrasound system or part of a pop-out panel. An operator removes an ultrasound transducer probe from a probe holder 30 and places the probe in contact with a patient to be scanned. The transducer emits ultrasound energy which enters into a patient then is reflected back to the transducer.

The panel 30 includes a plurality of through-slots 34 of common size. In the embodiment shown, the slots 34 have circular openings at a top surface 36 and bottom surface 38 of the panel 30 and are cylindrical. In alternative embodiments the through slots are characterized as elliptical, square or other geometric-like cylinders. All through-slots 34 have a common defining dimension. In FIG. 2, the common defining dimension is the through-slot diameter at the top surface 36. Preferably, each slot 34 to receive a probe holder 32 has a common size. The circular cylindrical through-slots shown have a common diameter along the length of the through-slot. The axial length of the slots 34, however, may vary. In addition, the peripheral wall 40 dimensions of the through-slots may differ.

For the preferred embodiment, each through-slot includes a protrusion 42 along peripheral wall 40. Upon installation of a holder, the protrusion 42 is positioned within a channel of a probe holder. The protrusion 42 serves as a stop blocking the rotation of an inserted probe holder 32. Specifically, the protrusion limits the arc of rotation of the holder 32 between a first position and a second position. In other embodiments the protrusion 42 is positioned on the probe holder, while the channel for receiving the protrusion 42 is positioned along the through-slot. Specifically, the channel is a recessed channel along inner walls of panel 30 that define the through-slot.

Each through-slot 34 also includes a side opening 43. Each side opening 43 is defined at the periphery of the panel 30 and leads to the through-slot 34.

Probe Holder

Referring again to FIG. 2, the probe holder 32 is formed by a body 60 having a top surface 62, bottom surface 64, outer wall 66 and inner wall 68. The body 60 defines an inner cavity 70. The top surface defines a first opening 72 into the inner cavity 70. The bottom surface 64 defines a second opening 74 into the inner cavity 70. The outer wall 66 defines a third opening 76 into the inner cavity 70. The third opening 76 extends the axial length of the body 60 from the top surface 62 to the bottom surface 64 and from the first opening 72 to the second opening 74.

Figure 3:
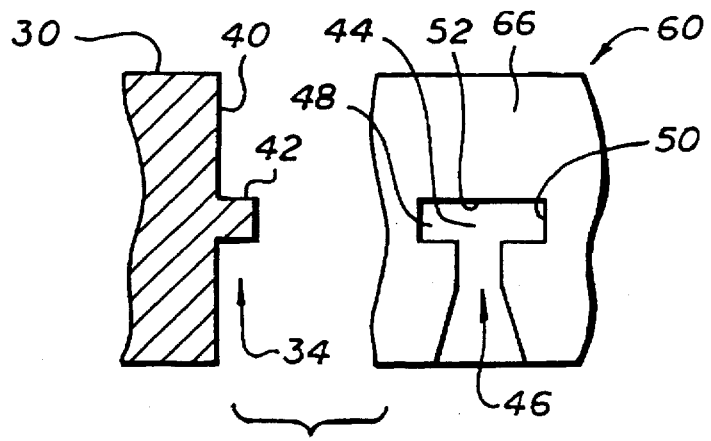
FIG. 3 is a partial planar view showing a protrusion in the panel through-slot and receiving channels in a probe holder of FIG. 2.

Referring to FIGS. 2 and 3, the holder body 60 defines a channel 44 for receiving the panel protrusion 42. The channel 44 extends along a partial circumference of the holder 32. When the protrusion 42 reaches one end 48 of the channel 44 in response to a rotational motion of the holder 32, the holder 32 is in a closed position. When the protrusion 42 reaches the other end 50 of the channel 44 in response to a rotational motion of the holder 32, the holder 32 is in an open position. In other embodiments the protrusion 42 is positioned on the probe holder 32, while the channels 44, 46 for receiving the protrusion 42 are positioned along the through-slot 34. Specifically, the channels 44, 46 are recessed channel along inner walls 40 defining the through-slot 34.

The probe holders 32 fit into any through-slot 34 allowing an operator to arrange and re-arrange the holders 32 according to desired preference.

To insert the probe holder 32 into the through-slot 34, the holder 32 is oriented with a channel 46 aligned with the protrusion 42. As the holder 32 is inserted into the through-slot, the protrusion 42 progresses along channel 46 into channel 44. A side wall 52 of channel 44 defines a stop preventing further insertion of the holder 32 into the through-slot 34.

According to the preferred embodiment, the body 60 rotates within the through-slot 34. For through-slots having an elliptical, square or other-shaped opening preventing rotation, the holder includes an upper body portion defines to fit the through-slot opening shape. The holder also includes lower portion which is smaller than the opening. To adjust such holder, the holder is lifted to free the upper portion from the confines of the through-slot opening. The holder then is rotated. The lower portion of the holder is not restricted from rotation between a holder open position and a holder closed position.

Figure 4:
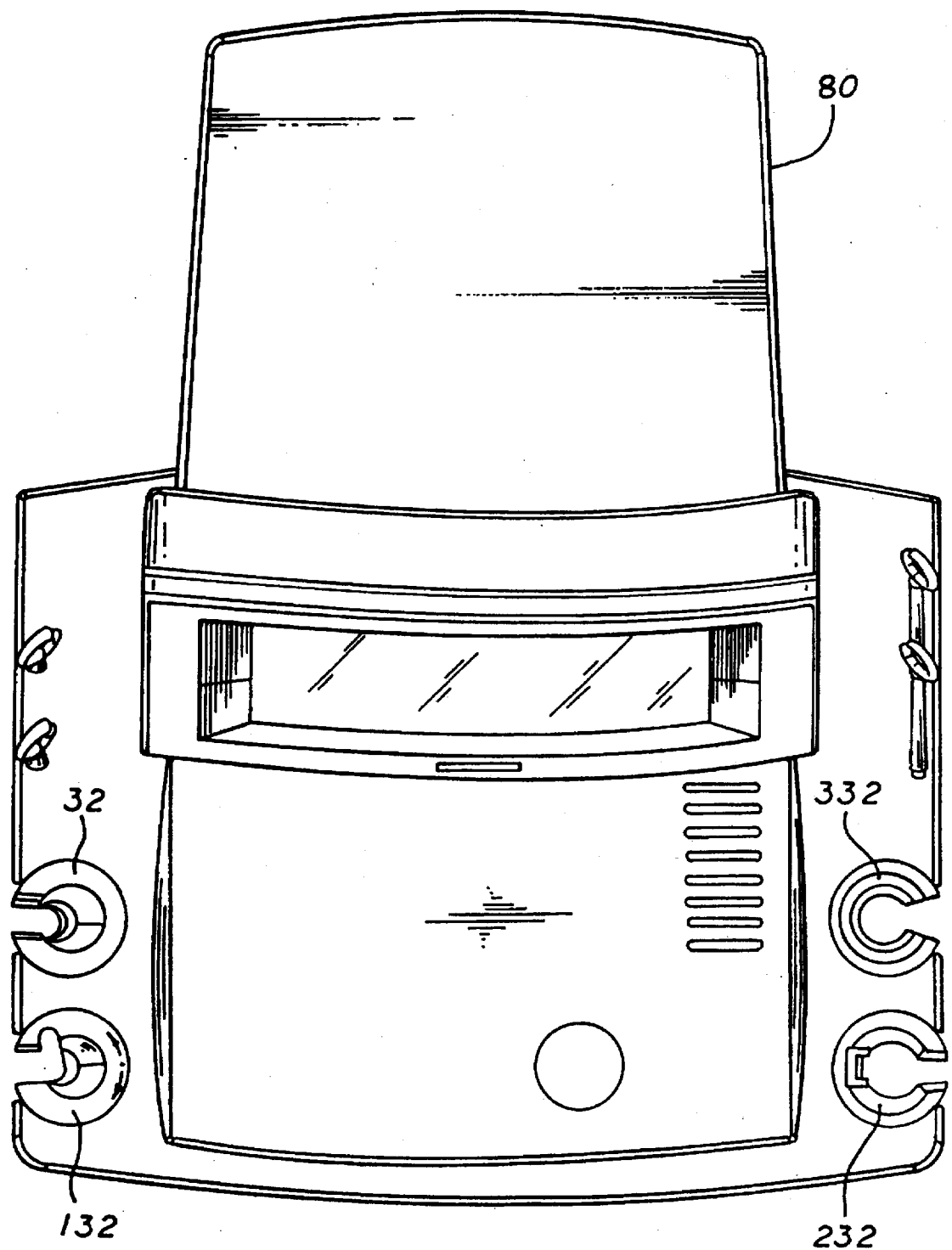
FIG. 4 is a top view of an ultrasound system showing a plurality of probe holders in the open position according to an embodiment of this invention.
Figure 5:
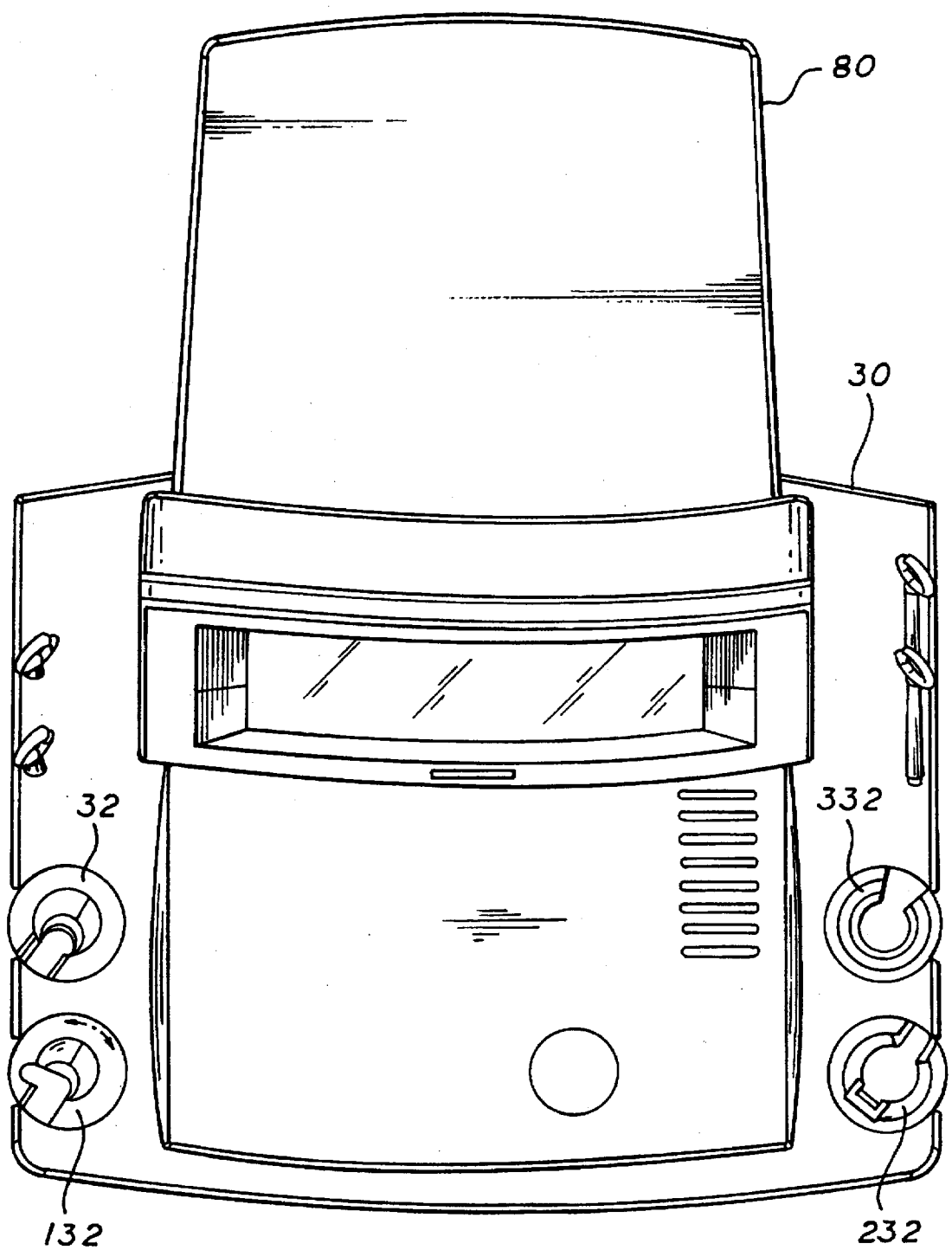
FIG. 5 is a top view of an ultrasound system showing the plurality of probe holders of FIG. 4 in the closed position according to an embodiment of this invention.

FIG. 4 shows a top view of an ultrasound system 80 having four circular cylindrical through-slots 34 along the periphery of panel 30. The through-slots each contain a probe holder according to alternative embodiments of this invention. Each probe holder is shown in the open position. The open position is defined as the position in which the third opening 76 of body 60 is aligned or otherwise exposed to the corresponding side opening 43 of panel 30. While in the open position, the cord 18 of a transducer probe 16 is moved by an operator through the side opening 43 and third opening 76 into the inner cavity 70 of the holder 32. With the cord within cavity 70, the body 60 is rotated or otherwise adjusted or manipulated into a closed position. In one embodiment, the body 60 is rotated moving the third opening 76 out of alignment with the corresponding side opening 43. The holder 32 is fully closed when the third opening does not open to the open environment, but instead opens to the inner wall 40 of the through-slot 34. FIG. 5 shows a top view of the ultrasound system 80 with the probe holders of FIG. 4 moved to the closed position.

Alternative Embodiments

FIG. 6 shows a probe holder 32 according to one embodiment of this invention. The probe holder 32 second opening 74 extends at the bottom surface 64 (See FIG. 2) from the third opening 76 radially inward.

FIG. 7 shows a probe holder 132 according to another embodiment of this invention. The probe holder 132 is similar to the probe holder 32 and has like parts labelled with like numbers. The probe holder 132 also defines a groove 142 extending axially from the top surface 62 to the bottom surface 64. The groove 142 is open to the inner cavity 70. The second opening 74 extends from the third opening 76 radially inward as holder 32, but also extends to the groove 142. A wall 144 defining the second opening is generally L-shaped. In one embodiment, the holder 132 slants radially inward along an axial direction, (i.e., from top surface 62 to bottom surface 64.

FIG. 8 shows a probe holder 232 according to another embodiment of this invention. Like parts relative to holder 32 are labeled with like numbers. The holder 132 is contoured along inner walls 66 to receive a probe head. Ridges 146, 147, 148, 149 are defined along inner walls 68 for defining an area for capturing the probe head. Each ridge 146–149 extends along at least a portion of the axial length of the wall 68. When the probe is inserted to the probe holder, the probe cord slides through the inner cavity 70. Once the probe head comes to rest between the ridge 146–149, the probe is rotated by the operator. The action on the probe rotates the probe holder 132 relative to the through-slot 34 into a closed position. The ridges serve to limit the rotation of the probe 16 relative to the probe holder 32 allowing the probe to move the probe holder.

The probe holder 232 includes an extension arm 234. A distal end 236 of arm 234 extends beyond the bottom surface 64. The distal end defines a ridge 238. During insertion the holder 232 is pushed into the through-slot 34 until the ridge 238 passes below a lower surface of the panel 30. The ridge snaps outward axially locking the holder 232 in place. The holder 232 includes two arms 234 located at opposing circumferential positions of the body 60 outer wall.

Figure 9:
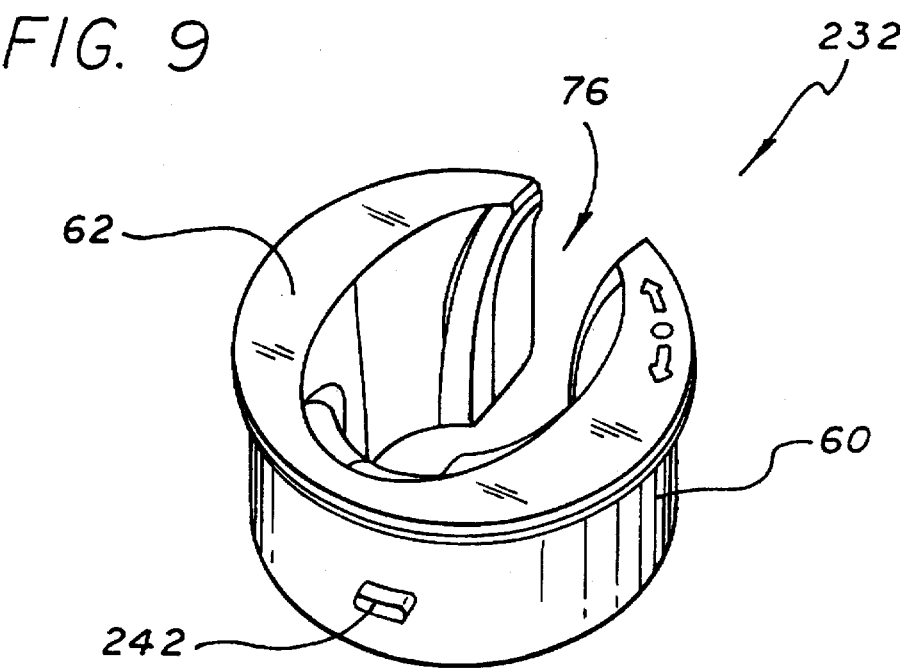
FIG. 9 is another perspective view of the probe holder of FIG. 8.

FIG. 9 shows another view of the probe holder 232. Note that in the embodiment illustrated the protrusion 242 analogous to protrusion 42 is located on the probe holder 232. Accordingly, the channels 44, 46 for receiving such protrusion 242 are defined along the walls 40 of the through-slot.

Figure 10:
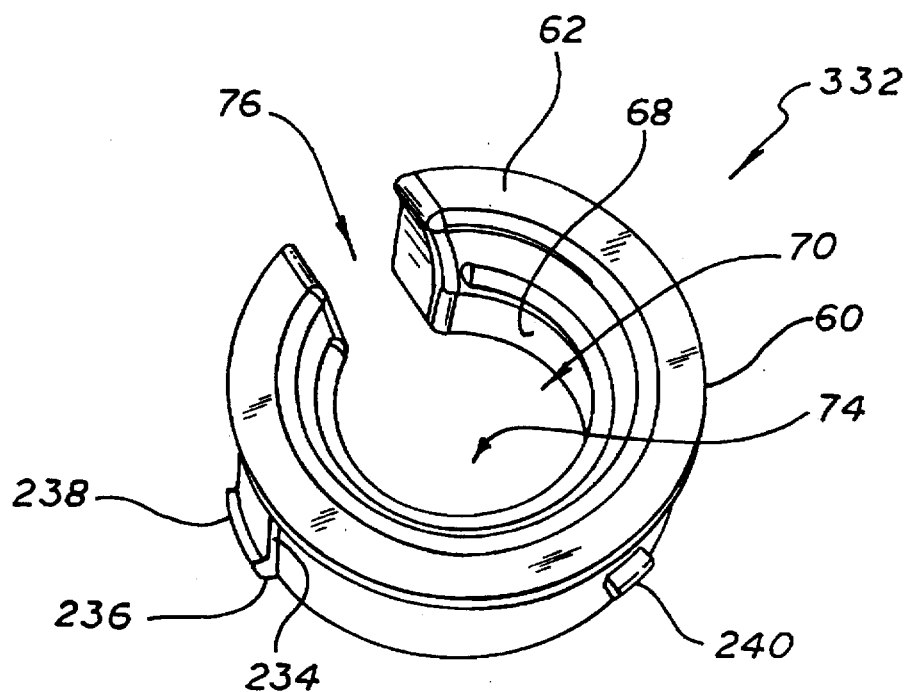
FIG. 10 is a perspective view of a probe holder according to another embodiment of this invention.

FIG. 10 shows a probe holder 332 according to another embodiment of this invention. Like parts relative to holder 32 and 232 are labeled with like numbers. The holder 332 includes a ring 152 extending radially inward from the inner wall 68. The ring 152 blocks the path of a probe head from passing through the inner cavity. The holder 332 is beneficial for narrow-headed probes that would slide through the inner cavities of holders 32, 132 and/or 232. In other embodiments, the ring 152 is instead a plurality of protrusions or teeth extending radially-inward to perform the same function.

Figure 11:
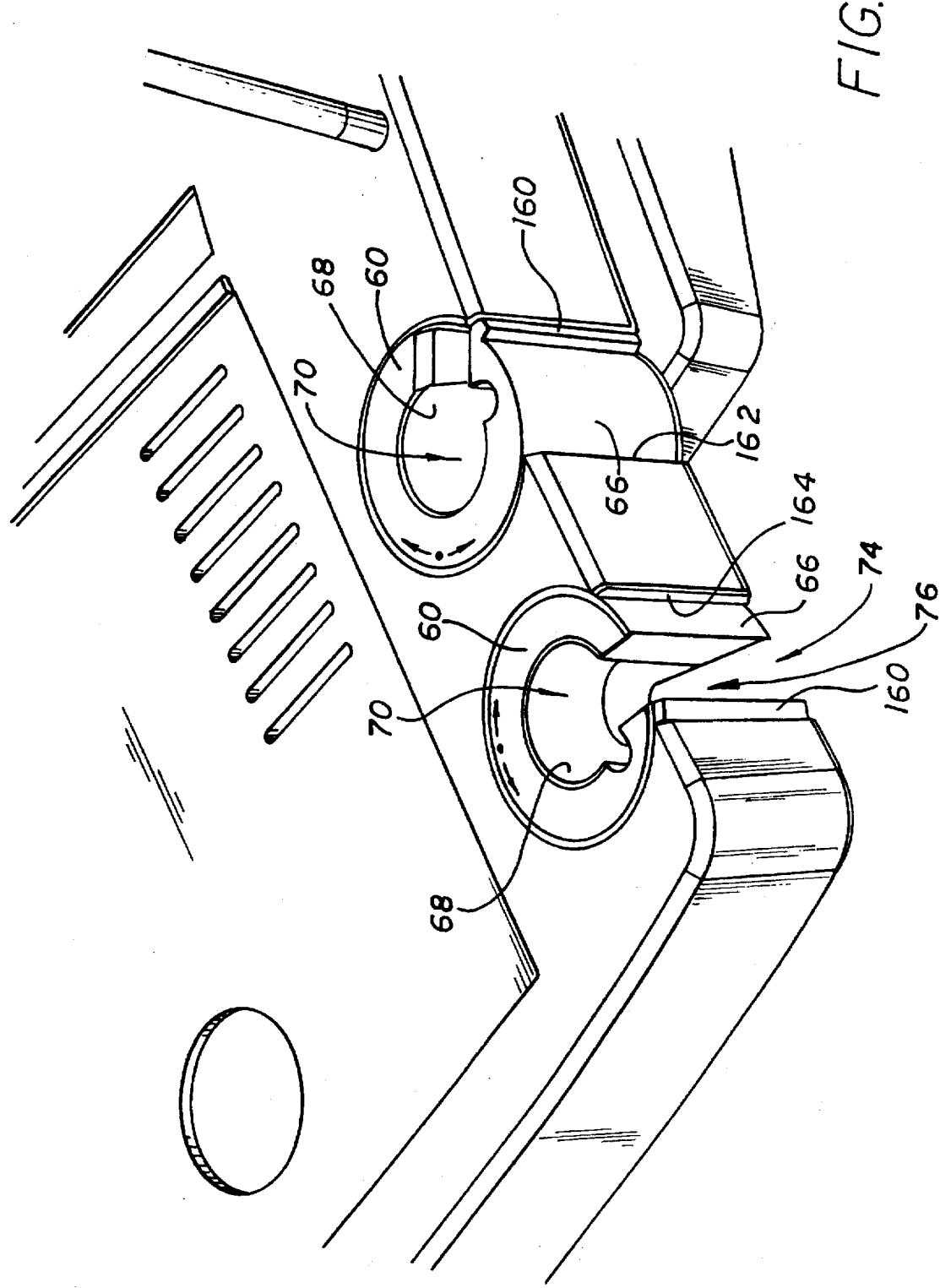
FIG. 11 is a partial perspective view of an ultrasound panel and probe holder according to another embodiment of this invention.

FIG. 11 shows a probe holder 32 inserted into a through-slot 34 of a panel 30. In this embodiment, a ridge 160 protruding from the outer wall 66 of the body 60 serves to limit the arc of rotation of the body 60, (i.e., instead of the protrusion 42). The protrusion 42 is omitted from such embodiment. The ridge 66 is located in the vicinity of the third opening 76, preferably adjacent to the opening 76. Upon insertion of the body 60 into the through-slot 34, the ridge 66 is located within the side opening 43 (See FIG. 2) of the panel 30. when the body 60 is rotated, the ridge 160 is moved with the body. The ridge 160 is blocked by a first wall 162 defining the panel side opening 43 at one extreme position, (e.g., open position). Similarly, the ridge 160 is blocked by a second opposing wall 164 defining the panel side opening 43 at an opposite extreme position, (e.g., closed position).

In yet other embodiments, the holder 32 instead is a cup without a second opening 74 or third opening 76. Such cup is insertable, rotatable and removable as enabled by the protrusion 43 and channels 44, 46 (See FIG. 3). The cup serves for holding a tube of gel or other supply for easy access by an ultrasound operator.

What is claimed is:

1. An ultrasound transducer probe holder removably received into a through-slot of an ultrasound system panel, the panel having an inner wall defining the through-slot and a side opening into the through-slot, the holder comprising:

a body which defines an inner cavity, the body having a top surface defining a first opening to the inner cavity and a bottom surface defining a second opening to the inner cavity, the body having an outer sidewall between the top surface and bottom surface, the sidewall defining a third opening to the inner cavity, the third opening extending from the top surface to the bottom surface, the third opening adjoining the first opening and the second opening, the body movable between an open position in which the body's third opening is aligned to the panel's side opening and a closed position in which the body's third opening is exposed to the panel's inner wall.

2. The holder of claim 1, in which the body is removable from the through-slot while the body has a prescribed orientation between the open position and the closed position.

3. The holder of claim 1 in which the body is rotatable between the open position and closed position.

4. The holder of claim 1, in which the body and panel inner wall define: a protrusion and a channel extending circumferentially for receiving the protrusion, the protrusion extending into the channel and limiting the relative range of motion between the body between and the through slot.

5. The holder of claim 1, in which the inner cavity is defined by inner walls of the body, the inner walls further defining a groove within the inner cavity, the groove extending from the top surface to the bottom surface.

6. The holder of claim 1, in which the inner cavity is defined by inner walls of the body, the inner walls further defining a plurality of ridges at the inner cavity, the plurality of ridges limiting rotation of a head portion of the probe relative to the inner cavity.

7. The holder of claim 6 in which rotation of an inserted probe having the head portion oriented between the plurality of ridges causes the body to rotate relative to the through-slot.

8. The holder of claim 1 in which the inner cavity is defined by inner walls of the body, the body further comprising a protrusion within the inner cavity for limiting the through path of a probe head portion through the inner cavity.

9. An ultrasound transducer probe holder removably received into a through-slot of an ultrasound system panel, the panel having an inner wall defining the through-slot and a side opening into the through-slot, the holder comprising:

a body which defines an inner cavity, the body having a top surface defining a first opening to the inner cavity and a bottom surface defining a second opening to the inner cavity, the body having an outer sidewall between the top surface and bottom surface, the sidewall defining a third opening to the inner cavity along a length of the sidewall from the top surface to the bottom surface, the body movable between an open position in which the body's third opening is aligned to the panel's side opening and a closed position in which the body's third opening is exposed to the panel's inner wall, the body further comprising a ridge along the outer sidewall, the ridge extending into the panel's side opening while the body is inserted into the through-slot, the ridge limiting the body's range of motion between the open position and the closed position.

10. An apparatus for securing a plurality of ultrasound transducer probes, comprising:

a panel defining a plurality of commonly-sized through-slots along the panel periphery, the panel further defining a plurality of side openings, each one side opening exposing a corresponding one of said plurality of through-slots;

a plurality of removable probe holders, each one of the plurality of probe holders receivable into any of the plurality of through slots enabling re-arrangement of the plurality of probe holders among the plurality of through-slots;

each one of the plurality of probe holders, comprising:
a body which defines an inner cavity, the body having a top surface defining a first opening to the inner cavity and a bottom surface defining a second opening to the inner cavity, the body having an outer sidewall between the top surface and bottom surface, the sidewall defining a third opening to the inner cavity along a length of the sidewall from the top surface to the bottom surface, the body movable between an open position in which the body's third opening is aligned to a given panel side opening and a closed position in which the body's third opening is exposed to an inner wall of the given panel.

11. A method of securing a transducer probe at holder removably received into a through-slot of an ultrasound system panel, the panel having an inner wall defining the through-slot and a side opening into the through-slot, the holder comprising a body defining an inner cavity and having a top surface defining a first opening to the inner cavity and a bottom surface defining a second opening to the inner cavity; the body having a sidewall between the top surface and bottom surface, the sidewall defining a third opening to the inner cavity along a length of the sidewall from the top surface to the bottom surface, the body movable between an open position in which the body's third opening is aligned to the panel's side opening and a closed position in which the body's third opening is exposed to the panel's inner wall, the method comprising the steps of:

inserting the holder into the through-slot;

moving the holder into the open position;

passing a cord of the transducer probe through the panel's side opening and body's third opening into the body's inner cavity while the holder is on the open position; and moving the holder into the closed position.

* * * * *